(12) United States Patent
Girotti et al.

(10) Patent No.: US 7,524,788 B2
(45) Date of Patent: Apr. 28, 2009

(54) PROCESS FOR THE ALKYLATION OF AROMATIC COMPOUNDS

(75) Inventors: Gianni Girotti, Novara (IT); Franco Rivetti, Milan (IT); Stefano Ramello, Novara (IT)

(73) Assignee: Polimeri Europa S.p.A., Brindisi (IT)

( * ) Notice: Subject to any disclaimer, the term of this patent is extended or adjusted under 35 U.S.C. 154(b) by 308 days.

(21) Appl. No.: 10/499,345

(22) PCT Filed: Dec. 18, 2002

(86) PCT No.: PCT/EP02/14817

§ 371 (c)(1),
(2), (4) Date: Nov. 16, 2004

(87) PCT Pub. No.: WO03/053892

PCT Pub. Date: Jul. 3, 2003

(65) Prior Publication Data

US 2005/0075239 A1      Apr. 7, 2005

(30) Foreign Application Priority Data

Dec. 20, 2001    (IT)    ............... MI2001A2707

(51) Int. Cl.
*B01J 29/06*    (2006.01)
(52) U.S. Cl. .................. 502/64; 502/60; 502/63; 502/65; 502/66; 502/71; 502/73; 502/74; 502/77; 502/78; 502/79
(58) Field of Classification Search ............. 502/60, 502/63, 64, 65, 66, 71, 73, 74, 77, 78, 79
See application file for complete search history.

(56) References Cited

U.S. PATENT DOCUMENTS

| | | | |
|---|---|---|---|
| 2,410,553 A | 11/1946 | Schmerling et al. | |
| 2,412,230 A | 12/1946 | Schaad | |
| 2,904,607 A | 9/1959 | Mattox et al. | |
| 3,121,754 A | 2/1964 | Mattox et al. | |
| 3,917,543 A * | 11/1975 | Bolton et al. ............... 502/66 |
| 3,948,760 A * | 4/1976 | Gring ................... 208/111.1 |
| 4,283,583 A | 8/1981 | Velenyi et al. | |
| 4,448,998 A * | 5/1984 | King ........................ 564/488 |
| 5,234,876 A | 8/1993 | Swaroop et al. | |
| 5,358,916 A * | 10/1994 | Shiokawa et al. ............ 502/65 |
| 5,672,799 A | 9/1997 | Perego et al. | |
| 5,968,466 A | 10/1999 | Kharas et al. | |
| 6,512,153 B1 | 1/2003 | Cappellazzo et al. | |

FOREIGN PATENT DOCUMENTS

| | | |
|---|---|---|
| CN | 1325837 | 12/2001 |
| EP | 687500 | 12/1995 |
| EP | 1069100 | 1/2001 |
| JP | 341038 | 2/1991 |
| JP | 1135498 | 2/1999 |
| WO | 01/62692 | 8/2001 |

OTHER PUBLICATIONS

P.H. Emett, et al., "The Catalytic Hydrogenation of Benzene over Metal Catalysts", The Journal of the American Society, vol. LXV, Jun. 1943, pp. 1029-1035.
Sigmund M. Csicsery, "Shape-selective catalysis in zeolites", 202, Zeolites, Jul. 1984, vol. 4, pp. 1-12.
Brent M. Lok, et al., "Silicoaluminophosphate Molecular Sieves: Another New Class of Microporous Crystalline Inorganic Solids", Journal of the American Chemical Society, 1984, 106, pp. 6092-6093.

* cited by examiner

*Primary Examiner*—Elizabeth D Wood
(74) *Attorney, Agent, or Firm*—Oblon, Spivak, McClelland, Maier & Neustadt, P.C.

(57) ABSTRACT

Process for preparing alkylated aromatic compounds which comprises reacting an aromatic compound with a ketone and hydrogen in the presence of a catalytic composition comprising a solid acid material and copper. A preferred aspect is to use a catalytic composition also containing one or more elements selected from elements of groups IIIA, IVA, IIIB, IVB, VB, VIB, VIIB, group VIII limited to Fe, Ru and Os, and of the series of lanthanides. A particularly preferred aspect is to use a catalytic composition containing one or more elements selected from elements of groups IIIA and VIB.

17 Claims, 2 Drawing Sheets

PROCESS FOR THE ALKYLATION OF AROMATIC COMPOUNDS

The present invention relates to a process for the alkylation of aromatic compounds which comprises reacting an aromatic compound with a ketone and hydrogen in the presence of a catalytic composition comprising a solid acid material and copper. A preferred aspect is for the catalytic composition to also contain one or more elements selected from elements of groups IIIA, IVA, IIIB, IVB, VB, VIB, VIIB, group VIII limited to Fe, Ru and Os, and of the series of lanthanides. A particularly preferred aspect is for the catalytic composition to contain one or more elements selected from elements of groups IIIA and VIB.

In particular, the invention relates to a process for the production of cumene starting from the reagents acetone, benzene and hydrogen, which are reacted in a single reaction step in the presence of said catalytic system.

Even more specifically, the invention relates to an alkylation process of an aromatic hydrocarbon, preferably benzene, with acetone and hydrogen in the presence of a catalytic composition containing a solid acid material, copper and one or more elements selected from Cr and Al, wherein the solid acid material comprises or consists of a zeolite, preferably zeolite beta.

The new preparation of cumene according to the present invention can be used in particular in a production process of phenol comprising the following steps:
(a) reacting benzene, acetone and hydrogen in the presence of the catalytic system according to what is specified above, comprising a solid acid material and copper,
(b) oxidizing the cumene to cumene hydroperoxide,
(c) treating the cumene hydroperoxide with acids to obtain a re-arrangement to phenol and acetone.

A preferred aspect is for the catalytic composition used in step (a) to also contain one or more elements selected from elements of groups IIIA, IVA, IIIB, IVB, VB, VIB, VIIB, group VIII limited to Fe, Ru and Os, and of the series of lanthanides. A particularly preferred aspect is for the catalytic composition of step (a) to contain one or more elements selected from elements of groups IIIA and VIB.

The acetone which is formed in step (c) can be recycled to step (a) for the synthesis of cumene.

According to what is specified above, the catalytic composition used in step (a) preferably comprises zeolite beta and copper. A particularly preferred aspect is to use in step (a) a catalytic composition containing zeolite beta, Cu and a metal selected from Cr and Al.

Cumene or isopropyl benzene is an important intermediate in the basic chemical industry mainly used as precursor for the production of phenol, in turn useful as intermediate in the preparation of caprolactam from which nylon is produced.

The industrial synthesis of phenol comprises the alkylation steps of benzene to cumene, the oxidation of cumene to cumyl hydroperoxide and the subsequent rearrangement to give phenol and acetone.

As far as the alkylation of benzene to cumene is concerned, catalysts based on phosphoric acid and infusorial earth for fixed bed reactors or $AlCl_3$ in slurry, and propylene as alkylating agent, are still widely used in the petrochemical industry.

These processes however create problems relating to environmental impact and safety: the use of these catalysts, in fact, is particularly problematical due to corrosion, the by-production of toxic organic products and the disposal of the exhausted catalysts.

In 1965, however, the preparation of cumene was described for the first time, using zeolite X or zeolite Y as catalyst (Minachev, Kr. M., et al, Neftekhimiya 5 (1965) 676). The use of zeolites with a faujasitic structure for the alkylation of benzene with light olefins such as propylene, was subsequently described by Venuto et al. (J. Catal. 5, (1966) 81).

U.S. Pat. No. 4,292,457 describes the use of ZSM-5 type zeolites for alkylating benzene with propylene.

Excellent results in terms of industrial application have been obtained in the synthesis of cumene using zeolites with a beta-type structure, as described in EP 432814, and in particular using catalysts comprising zeolite beta according to what is described in EP 687500 and in EP 847802.

Once cumene has been obtained, it is transformed into phenol by means of an oxidation step to cumene hydroperoxide, followed by an acid treatment step which causes the breakage of the peroxide bond with the formation of phenol and acetone.

The synthesis of phenol via cumene, on which most industrial plants existing throughout the world for the production of phenol, are based, leads to the co-production of a quantity of acetone equal to 0.61 kg per kg of phenol.

Phenol is mainly used in the production of bisphenol A (about 35%), phenolic resins (about 35%), caprolactam (about 15%), aniline, alkylphenols, xylenols and other products, whereas acetone is mainly used in the production of methylmethacrylate (about 45%), bisphenol A (about 20%), solvents (about 17%) and methylisobutylketone (about 8%).

There is therefore an unbalanced situation, at least potential, in the request for phenol and acetone, intrinsically deriving from their co-production, which does not allow a modulation in their supply in relation to the growth margins of the different sectors and outlet markets for the two products.

New processes based on the re-use of acetone—co-produced with phenol—in the upstream synthesis of cumene, have been proposed to avoid this situation. In EP 361755, the propylene used as alkylation agent of benzene for the synthesis of cumene is obtained, either totally or partially, starting from acetone, after reduction with hydrogen to isopropanol and subsequent dehydration to propylene.

The re-use of the possible excess acetone for the re-production of propylene according to the method described above, is extremely onerous, particularly due to the high number of steps associated with the chemical reduction transformations to isopropyl alcohol and the subsequent dehydration of the alcohol to propylene.

An alternative which reduces the number of chemical transformations necessary for the re-use of acetone consists in the direct use of isopropanol, obtained by the reduction of acetone with hydrogen, as alkylation agent of benzene in the synthesis of cumene, as described for example in EP 1069100.

The direct alkylation of benzene with isopropanol, obtained by the reduction of acetone co-produced with phenol, represents an improvement, from an industrial point of view, with respect to the option which involves the re-production of propylene to be used as alkylation agent of benzene, but the best solution, from an industrial and process point of view, would obviously consist of the direct use of acetone as alkylation agent of benzene, in the presence of hydrogen, in the synthesis of cumene.

A catalytic system has now been found, which is capable of promoting the synthesis of cumene starting directly from the reagents acetone, benzene and hydrogen.

The cumene, obtained according to the industrial process claimed herein, can be used for the subsequent production of phenol by means of oxidation to cumene hydroperoxide and the subsequent rearrangement of the hydroperoxide to phenol and acetone. The acetone thus obtained, can in turn be used for the synthesis of cumene by the direct alkylation of benzene with acetone and hydrogen carried out according to the industrial process claimed herein.

The object of the present invention therefore relates to a process for the alkylation of aromatic compounds which comprises reacting an aromatic compound with a ketone and hydrogen in the presence of a catalytic composition comprising a solid acid material and copper. A preferred aspect is for the catalytic composition to also additionally contain one or more elements selected from elements of groups IIIA, IVA, IIIB, IVB, VB, VIB, VIIB, group VIII limited to Fe, Ru and Os, and of the series of lanthanides. A particularly preferred aspect is for the catalytic composition to contain one or more elements selected from elements of groups IIIA and VIB. The aromatic compound is preferably benzene.

The ketone is preferably acetone.

More specifically, the object of the present invention relates to a process for the alkylation of benzene to give cumene which comprises reacting acetone, benzene and hydrogen, which are reacted in a single reaction step, in the presence of a catalytic system comprising a solid acid material and copper. A preferred aspect is for the catalytic composition used for the alkylation of benzene to cumene to additionally contain one or more elements selected from elements of groups IIIA, IVA, IIIB, IVB, VB, VIB, VIIB, group VIII limited to Fe, Ru and Os, and of the series of lanthanides. A particularly preferred aspect is for the catalytic composition to contain one or more elements selected from elements of groups IIIA and VIB, preferably Cr or Al.

The alkylation process, object of the present invention, allows the preparation of phenol from cumene to be considerably simplified; it is not necessary in fact to first effect the chemical reduction transformation of acetone to isopropanol as described for example in U.S. Pat. No. 5,160,497, the subsequent chemical dehydration transformation of isopropanol to propylene as described for example in U.S. Pat. No. 5,017,729 and consequently the subsequent chemical alkylation transformation of benzene with propylene as described for example in EP 439632.

The chemical transformations described above are normally carried out under somewhat different reaction conditions for each of the reactions in question and in the presence of equally different catalysts.

The catalytic system used in the process of the present invention allows all the chemical transformations necessary for the preparation of cumene starting from the reagents acetone, benzene and hydrogen, to be contemporaneously carried out in a single reaction step, maximizing the yield to cumene and minimizing the secondary reactions of the various reagents, intermediates and products.

Particularly significant secondary and undesired reactions for determining the overall yield which could be expected by experts in the field are the parallel reduction reaction of benzene with hydrogen to cyclohexene, cyclohexane and hexane, the parallel condensation reaction of acetone to 4-methyl-3-penten-2-one and the subsequent reactions of these by-products with the various reagents and products of the main reactions such as for example the alkylation of benzene to phenylcyclohexane due to the cyclohexene and reduction of 4-methyl-3-penten-2-one to 4-methyl-2-pentanone and 4-methyl-2-pentanol due to the hydrogen.

The catalytic system used in the process of the present invention unexpectedly allows the conversion of the reagents to be oriented towards the desired product, reducing the formation of undesired products to the minimum.

The catalytic system used in the alkylation process of aromatic compounds, in particular benzene, which is object of the present invention, comprises a solid acid material and copper, wherein the copper is preferably in the form of an oxide.

According to a preferred aspect, the catalytic composition also contains one or more elements selected from elements of groups IIIA, IVA, IIIB, IVB, VB, VIB, VIIB, group VIII limited to Fe, Ru and Os, and of the series of lanthanides. These elements of groups IIIA, IVA, IIIB, IVB, VB, VIB, VIIB, group VIII limited to Fe, Ru and Os, and of the series of lanthanides, are also preferably in the form of oxides. In particular, copper and these elements can be contained in the catalytic composition in the form of a mixed oxide.

According to a particularly preferred aspect, the catalytic composition contains one or more elements selected from the elements of groups IIIA and VIB. In accordance with what is specified above, these elements of groups IIIA and VIB are preferably in the form of oxides. In particular, copper and these elements can be contained in the catalytic composition in the form of a mixed oxide.

A particularly preferred aspect of the present invention is to use catalytic compositions containing copper and an element selected from chromium and aluminum. In particular, copper and these elements can be contained in the catalytic composition in the form of a mixed oxide.

In particular, copper and chromium can be contained in the catalytic composition in the form of copper chromite. Copper chromite is represented by the empirical formula CuO—$CuCr_2O_4$. $CuCr_2O_4$ is known as C.A.S. R.N. 12018-10-9 and is described in "Gmelins Handbuch der Anorganischen Chemie, $8^{th}$ ed., Vol. Kupfer, part B, Installment 3, system number 60, page 60". In the process of the present invention, commercially available materials called copper chromite, can be used, containing Cu (II) and Cr (III), having varying proportions of CuO and $CuCr_2O_4$. These materials, which can optionally also contain small quantities of promoters such as Ba and Mn, are well known to experts in the field and are described for example in J. D. Stoupe, "An X-Ray Diffraction Study of the Copper Chromites and of the "Copper-Chromium Oxide" Catalyst" J. Am. Che. Soc., vol. 71, 1949, page 589; in A. Iimura et al., "Catalysis by "Copper Chromite", I, The effect of hydrogen Reduction on the composition, structure and catalytic activity for methanol decomposition", Bull. Chem. Soc. Jp., 56, 2203-2207 (1983); in R.B.C. Pillai, "A study of the pre-activation of a copper chromite catalyst", Catalysis Letters 26 (1994) 365-371.

Copper and aluminum can be contained in the catalytic composition used in the present invention in the form of the corresponding oxides.

In accordance with what is specified above, the catalytic composition containing copper chromite can contain, as promoters, barium and/or manganese, preferably in the form of oxides. The barium or manganese content is lower than 15% by weight with respect to the total weight of the composition and preferably ranges from 0.1 to 5% by weight. The weight percentages of barium and manganese refer to their content expressed as element.

The solid acid material contained in the catalytic composition used in the alkylation process of aromatic compounds of the present invention, in particular benzene, is preferably of a zeolitic nature and can contain one or more zeolitic materials. Zeolites which can be used are zeolite beta, zeolite Y, ZSM-12 and mordenite. These zeolites are described in "Atlas of zeolite structure types", Ch. Baerolocher, W. M. Meier and D. H. Olson, 2001, $5^{th}$ Edition, Elsevier. A preferred aspect is to use zeolite beta.

The zeolites are used in acid form, i.e. in the form in which all the negative charges deriving from the aluminum present in the structure are counterbalanced by hydrogen ions, or prevalently acid.

The zeolite beta used as component of the catalytic composition of the process according to the present invention corresponds to that described in U.S. Pat. No. 3,308,069, and is a porous crystalline material having the composition $$[(x/n)M(1\pm 0.1-x)TEA]AlO_2.ySiO_2.wH_2O$$

wherein n is the oxidation state of M, x is less than 1, y ranges from 5 to 100, w ranges from 0 to 4, M is a metal selected from those of groups IA, IIA, IIIA of the Periodic System or from transition metals and TEA is tetraethyl ammonium hydroxide.

A preferred aspect of the present invention is for the zeolite beta to be in acid form, i.e. in the form in which the $H^+$ ion has partially or totally substituted the metallic cations initially present.

This substitution is effected according to the known methods by means of an exchange with ammonium ions, washing and subsequent calcination.

The catalytic compositions which can be used in the alkylation process of the present invention, comprising a solid acid material and copper, can comprise suitable binding agents, for example oxides of groups IIIA, IVA and IVB. More preferably, the catalytic system can contain an oxide of Si or Al as binding carrier. Even more preferably, the catalytic system can contain γ-alumina as binding carrier.

γ-alumina is a known material and is commercially available in the form, preferred for the purposes of the invention, of the precursors bohemite or p-bohemite, transformed subsequently to γ-alumina during the preparation of the catalytic system, in the final calcination phase.

The binder is preferably used in a relative quantity by weight with respect to the catalytic system ranging from 5:95 to 95:5.

A particularly preferred aspect of the present invention is to use a catalytic system containing copper chromite and a beta-type zeolite, in its acid form. This composition can contain an inorganic binder in accordance with what is described above.

The copper is preferably contained in the catalytic composition of the present invention in a weight ratio of the metal with respect to the solid acid material ranging from 0.001 to 10, more preferably ranging from 0.01 to 2. When the catalytic composition contains one or more elements of groups IIIA, IVA, IIIB, IVB, VB, VIB, VIIB, group VIII limited to Fe, Ru and Os, and of the series of lanthanides, each element is preferably contained in a weight ratio of the metal with respect to the solid acid material ranging from 0.001 to 10, more preferably from 0.01 to 2.

The catalytic system used in the present invention, as described above, contains a solid acid component with an alkylation functionality and a metallic component containing copper and optionally one or more elements selected from elements of groups IIIA, IVA, IIIB, IVB, VB, VIB, VIIB, group VIII limited to Fe, Ru and Os, and of the series of lanthanides, with a hydrogenation functionality.

The catalytic system used in the present invention, containing a solid acid component and a metallic component containing copper and optionally one or more elements selected from elements of groups IIIA, IVA, IIIB, IVB, VB, VIB, VIIB, group VIII limited to Fe, Ru and Os and of the series of lanthanides, can be prepared, starting from the components described above, according to various practical combination procedures, each maintaining the specific characteristics listed above.

The catalytic system of the present invention can therefore consist of one or more distinct zones each containing a single functionality, either hydrogenation linked to the metallic component or alkylation linked to the acid component, in particular zeolitic, or both hydrogenation and alkylation functionalities having the characteristics described above.

Figure 1:
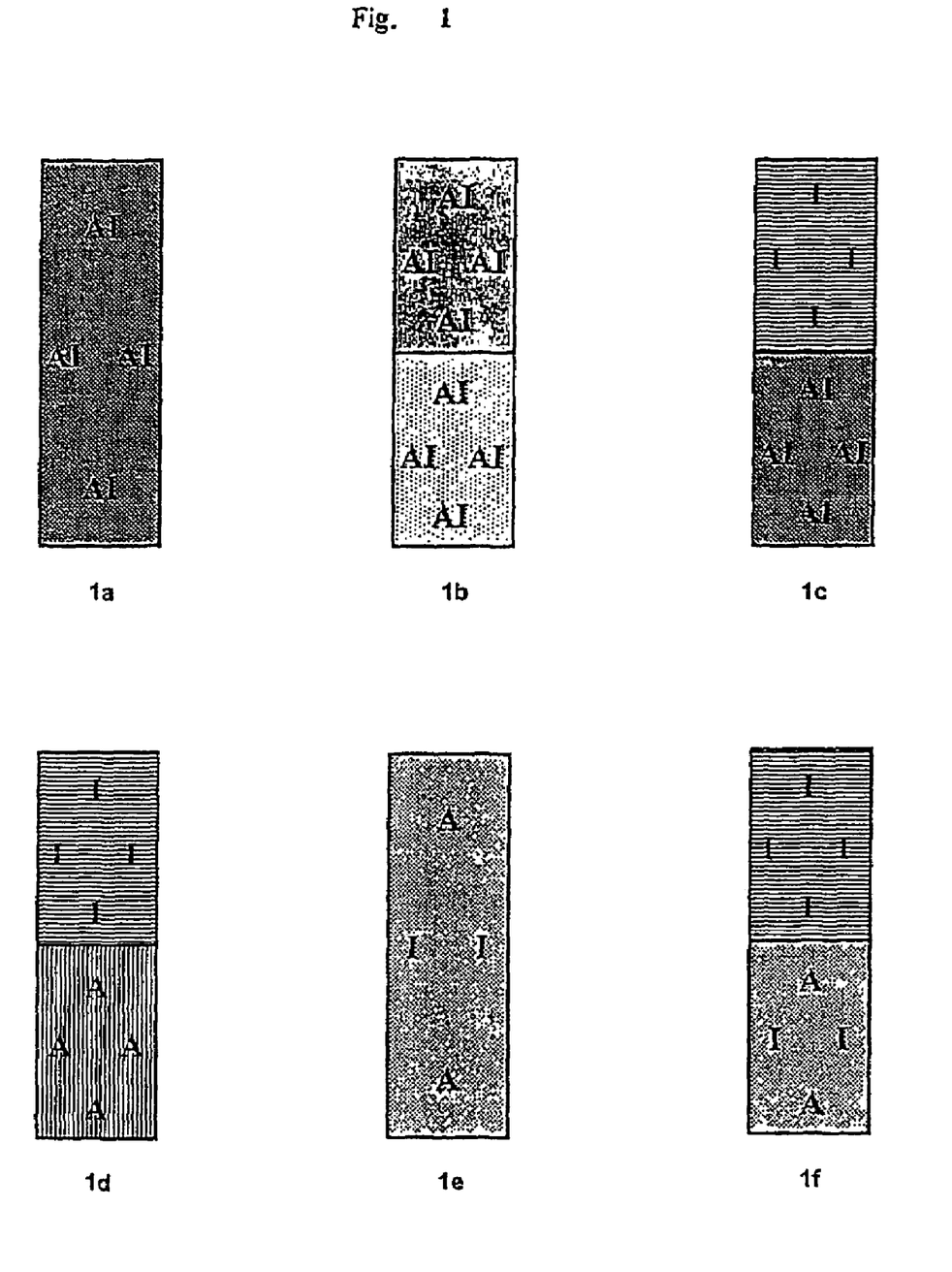

Examples of some of the various preparation procedures of the catalytic system are indicated below and are schematically represented in FIG. 1.

In this figure, I refers to the metallic component of the catalytic composition, containing copper and optionally one or more elements selected from elements of groups IIIA, IVA, IIIB, IVB, VB, VIB, VIIB, group VIII limited to Fe, Ru and Os, and of the series of lanthanides, said component having a hydrogenation functionality. When the metallic component contains copper alone, this is preferably in the form of an oxide. When the metallic component also contains an element selected from groups IIIA, IVA, IIIB, IVB, VB, VIB, VIIB, group VIII limited to Fe, Ru and Os, and of the series of lanthanides, it is also preferably in the form of an oxide. In this case, the component can be prepared for example by the mechanical mixing of the oxides. In the particular case in which the copper and the element or elements selected from groups IIIA, IVA, IIIB, IVB, VB, VIB, VIIB, group VIII limited to Fe, Ru and Os, are in the form of a mixed oxide, component I can be prepared for example according to the known coprecipitation techniques, or by melting the metal oxides present in the mixed oxide. The metallic component I preferably consists of copper chromite.

Again with reference to FIG. 1, A refers to the solid acid component, preferably zeolitic, containing the alkylation functionality. Zeolites which can be used are preferably zeolite beta, zeolite Y, ZSM-12 and mordenite. A preferred aspect is to use zeolite beta. The solid acid component, preferably zeolitic, can be used in a mixture with suitable binding agents, for example oxides of the elements of groups IIIA, IVA and IVB. The solid acid component A more preferably contains an oxide of Si or Al as binding carrier. Even more preferably, the solid acid component A contains γ-alumina as binding carrier. The zeolitic composition with binder can be prepared according to any of the known techniques. In the case of zeolite beta, it can be prepared, for example, as described in EP 687500 and EP 847802.

Again with reference to FIG. 1, AI refers to a composition containing both hydrogenation and alkylation functionalities. The composition indicated with AI can also comprise suitable binding agents, for example oxides of groups IIIA, IVA and IVB. The composition indicated with AI more preferably contains an oxide of Si or Al as binding carrier. Even more preferably, the composition AI contains γ-alumina as binding carrier. The composition AI can be prepared according to any of the techniques well known to experts in the field, such as for example a) impregnation, b) ion exchange or c) extrusion, described hereunder:

a) it is possible to operate for example by impregnating the solid acid material, preferably of a zeolitic nature, with an aqueous solution containing a copper salt and optionally a salt of an element selected from groups IIIA, IVA, IIIB, IVB, VB, VIB, VIIB, group VIII limited to Fe, Ru and Os, and of the series of lanthanides, drying and calcining the resulting product. Separate solutions for the copper salt and salt of the element of groups IIIA, IVA, IIIB, IVB, VB, VIB, VIIB, group VIII limited to Fe, Ru and Os, and of the series of lanthanides, can be used. The product obtained with this method can be optionally used in a mixture with a suitable binding agents, for examples oxides of groups IIIA, IVA and IVB, as described above. Alternatively, it is possible to operate by impregnating a mixture of solid acid material and binding agent with an aqueous solution containing a copper salt and optionally a salt selected from groups IIIA, IVA, IIIB, IVB, VB, VIB, VIIB, group VIII limited to Fe, Ru and Os, and of the series of lanthanides, drying and calcining the resulting product.

b) When the ion exchange technique is used, the solid acid material, preferably of a zeolitic nature, is for example put in an aqueous solution containing a copper salt and optionally a salt selected from groups IIIA, IVA, IIIB, IVB, VB, VIB, VIIB, group VIII limited to Fe, Ru and Os, and of the series of lanthanides, and the mixture left under stirring for a few hours. The solid in suspension is recovered by filtration, washed with demineralized water and dried: a solid acid material is obtained in exchanged form with copper ions and possibly ions of a metal selected from groups IIIA, IVA, IIIB, IVB, VB, VIB, VIIB, group VIII limited to Fe, Ru and Os, and of the series of lanthanides. The material obtained in this way can optionally be used in a mixture with a suitable binding agent, as defined above. Alternatively, a composition of a solid acid material and of suitable binding agents is used, which is subjected to the ion exchange process described above.

c) Alternatively, an extrusion process can be used, in which a mechanical mixture of the two components, i.e. the solid acid material, preferably zeolitic, and the metallic component, is paste-mixed with a peptizing acid solution, extruded, dried and calcined with any traditional method. The product obtained in this way can optionally be used in a mixture with a suitable binding agent, defined above. Alternatively, a mechanical mixture of the three components, i.e. the solid acid material, preferably zeolitic, the metallic component and a suitable binding agent, defined above, is subjected to an extrusion process. In accordance with what is specified above, the catalytic system can consist for example (FIG. 1a) of a sole AI composition zone containing both metallic and acid components, having alkylation and hydrogenation functionalities.

According to another embodiment, the catalytic system can consist for example (FIG. 1b) of two or more separate AI composition zones, each of which contain both the acid and metallic components, having alkylation and hydrogenation functionalities, wherein the composition of the single zones differs in terms of chemical nature and proportion between the alkylation and hydrogenation functionality. Each single zone of the AI composition is prepared with one of the known methods described above, and the zones are then assembled by stratification inside the reactor.

Another preparation procedure (FIG. 1c) of the catalytic system consists for example of two or more distinct zones, in one of which there is the metallic component I containing the catalytic hydrogenation function alone, whereas in the remaining zones there are one or more compositions AI with different combinations of the two components having alkylation and hydrogenation functionalities. Each single zone of the composition AI, containing two functionalities, is prepared with one of the known methods described above.

In another embodiment (FIG. 1d), the catalytic system consists for example of two or more distinct zones, in one of which there is component I containing the catalytic hydrogenation function alone, whereas in the subsequent zone there is component A, having an alkylation catalytic function. The acid component A, preferably zeolitic, can be used in a mixture with suitable binding agents, defined above.

In a further embodiment (FIG. 1e) the catalytic system consists for example of a single zone in which the two components of the catalytic composition, I and A respectively, mechanically mixed with each other, are arranged. Also in this case, the solid acid component A, preferably zeolitic, can be used in a mixture with suitable binding agents defined above.

In yet another embodiment (FIG. 1f), the catalytic system consists for example of two or more distinct zones, in one of which there is component I of the catalytic system containing the catalytic hydrogenation function alone whereas in the remaining zones there are one or more different pairs of components I and A, mechanically mixed, each of which contains the catalytic hydrogenation function alone or the catalytic alkylation function alone. Also in this case, the solid acid component, preferably zeolitic, can be used in a mixture with suitable binding agents defined above.

When the catalytic system has a zone containing the metallic component I alone, having a catalytic hydrogenating function, this is preferably the one which first comes into contact with the stream of reagents, in particular benzene, acetone and hydrogen. Furthermore, it is evident that, on the basis of the procedures described, a catalytic system characterized by the contemporaneous presence of a hydrogenation function, whose activity gradient decreases in one direction, and an alkylation function, whose activity gradient decreases in the opposite direction, can be easily produced by experts in the field, if desired.

The activity gradient of the hydrogenation function preferably decreases along the feeding direction and flow of the reagents, in particular acetone, benzene and hydrogen, whereas the activity gradient of the alkylation function decreases along the opposite direction and flow.

According to a preferred aspect of the alkylation process of the present invention, it is preferable to operate at a reaction temperature generally ranging from 50 to 350° C., preferably from 100 to 250° C. The pressure is generally equal to or higher than atmospheric pressure and preferably ranges from 1 to 50 bars. A molar ratio between aromatic hydrocarbon and ketone, in particular between benzene and acetone, is used in the feeding, not lower than 1 and preferably higher than 2. A molar ratio between hydrogen and ketone, in particular acetone, is used in the feeding not lower than 1 and preferably higher than 2. The catalytic composition is preferably pre-activated in a stream of hydrogen.

The reaction can be conveniently carried out in fixed bed catalyst reactors, containing one or more catalytic beds. The reagents can in this case all be fed to the reactor, in the desired proportions, to the first catalytic bed, or the feeding of the reagents or some of them can be partially fed to the different catalytic beds.

Some of the compositions prepared with the methods described above however can also be conveniently used in reactors different from fixed bed reactors.

Figure 2:
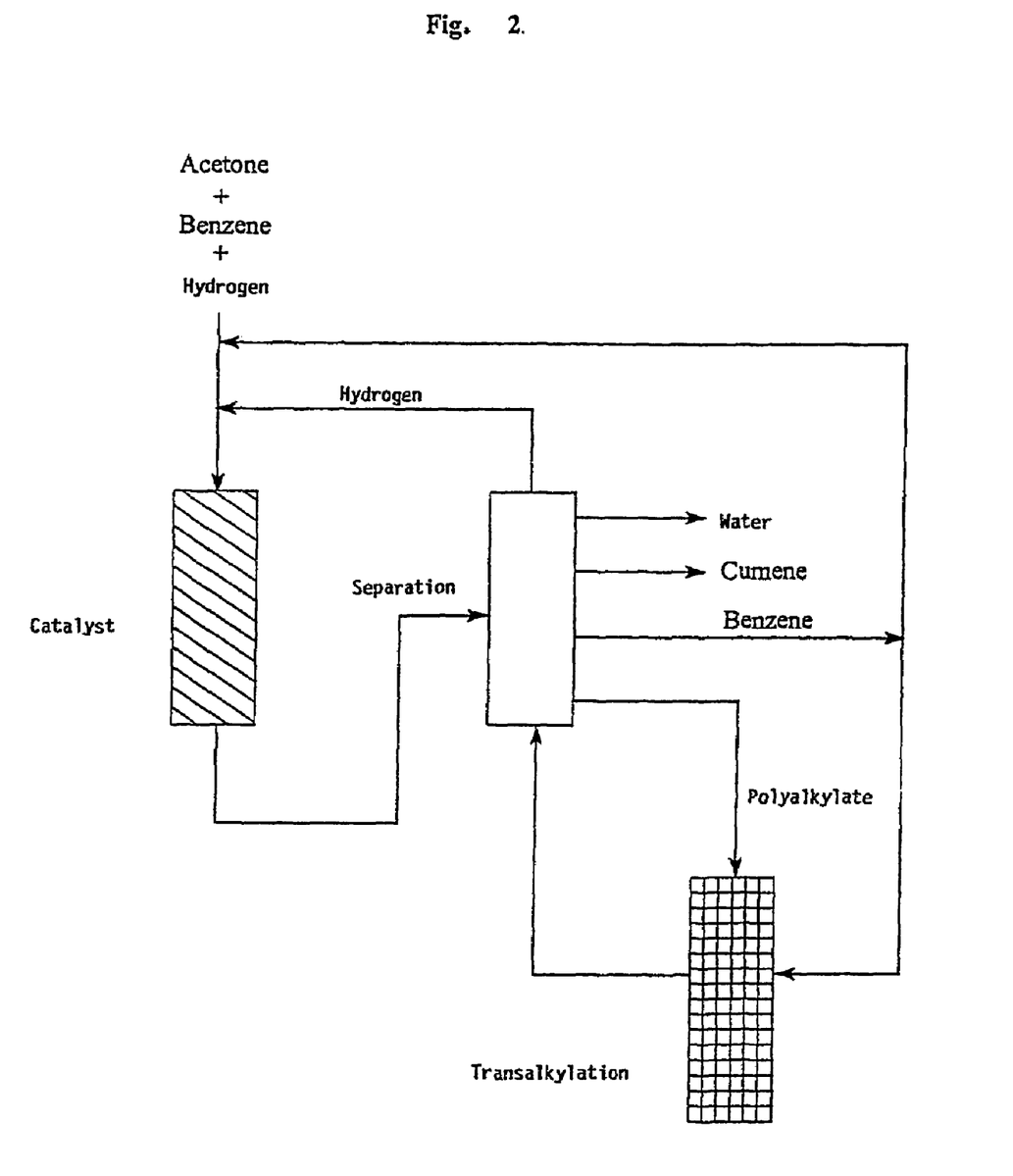

According to the process claimed herein and according to an embodiment of the invention, with reference to FIG. 2, benzene, acetone and hydrogen are reacted in a single step in the presence of the catalytic system described and under the conditions indicated for obtaining a reaction product which mainly contains isopropylbenzene, non-converted benzene, non-converted hydrogen, water and polyisopropylbenzenes.

The reaction product is fractionated in a separation section S using conventional separation methods, such as degassing, distillation or the demixing of liquids, to obtain a first fraction mainly containing hydrogen, a second fraction mainly containing water, a third fraction mainly containing benzene, a fourth fraction mainly containing isopropylbenzene and a fifth fraction mainly containing polyisopropylbenzenes.

The first fraction (containing hydrogen) is re-used in the reaction step with acetone and benzene, the second fraction (containing water) is removed from the process, the third fraction (containing benzene) is partly re-used in the reaction step with acetone and hydrogen and partly in a subsequent reaction step, called transalkylation step, where it is reacted with the fifth fraction (containing polyisopropylbenzenes) to produce again the desired product isopropylbenzene.

Transalkylation is a reaction which is well known in the state of the art and is carried out in the presence of a solid acid catalyst, preferably in the presence of a solid acid catalyst based on zeolites, more preferably in the presence of a solid acid catalyst based on beta-type zeolite as described for example in EP 687500 and in EP 847802.

The temperature conditions for the transalkylation reaction are selected from 100 to 350° C., the pressure is selected from 10 to 50 atm and the WHSV ranges from 0.1 to 200 hours$^{-1}$, as also described in EP 687500 and in EP 847802.

The transalkylation reaction product is fractionated using the conventional separation methods in the same separation section.

The third fraction coming from the separation section therefore contains non-converted benzene coming from both the alkylation step and the transalkylation step. The fourth fraction coming from the separation section contains cumene coming from both the alkylation step and the transalkylation step and the fifth fraction coming from the separation step contains polyisopropylbenzenes coming from both the alkylation step and the transalkylation step.

The cumene obtained according to the process, object of the present invention, can be used for the production of phenol by means of oxidation to cumene hydroperoxide and the subsequent rearrangement of the hydroperoxide to phenol and acetone.

A further object of the present invention therefore relates to a process for the production of phenol which comprises the following steps:
(a) reacting benzene, acetone and hydrogen in the presence of a catalytic system comprising a solid acid material and copper
(b) oxidation of cumene to cumene hydroperoxide
(c) rearrangement of the cumene hydroperoxide to phenol and acetone.

The acetone which is formed in step (c) can be recycled to the synthesis step (a) of cumene.

The catalytic composition used in step (a) also preferably contains one or more elements selected from elements of groups IIIA, IVA, IIIB, IVB, VB, VIB, VIIB, group VIII limited to Fe, Ru and Os, and of the series of lanthanides, and is in accordance with what is specified above with respect to the alkylation process of the present invention. The catalytic composition used preferably contains zeolite beta, copper chromite and optionally an inorganic binder.

The various passages for the oxidation of cumene to cumene hydroperoxide, the rearrangement of hydroperoxide to give phenol and acetone and the purification of phenol are well known in literature, as described for example in U.S. Pat. Nos. 5,160,497 and 5,017,729.

The oxidation step of cumene to cumene hydroperoxide can be carried out for example with molecular oxygen at a temperature ranging from 60 to 150° C. and at a pressure ranging from 1 to 10 kg-f/cm$^2$. It is preferable to operate in the presence of an initiator and an alkaline compound for the pH control.

The transformation step of cumene hydroperoxide to phenol and acetone is carried out in the presence of an acid, for example a strong acid such as sulfuric acid, or for example an exchange resin or a silico-alumina. At the end, the reaction mixture is concentrated to recover the acetone, which can then be recycled to the alkylation step (a). It can be clearly seen how a process for the production of phenol starting from hydrogen, oxygen and benzene, with the coproduction of water alone, can actually be effected by recycling the acetone to step (a).

According to a preferred aspect, at the end of the first step, after separating the desired product, cumene, by fractionation, which passes to the subsequent oxidation step, the remaining fraction of polyisopropylbenzenes is used in a separate step for a transalkylation reaction with benzene to recover other cumene.

The transalkylation reaction is carried out in the presence of zeolite beta or a catalyst based on zeolite beta, in particular prepared according to what is described in EP 687500 and EP 847802, which also describe the reaction conditions.

The catalytic composition of the present invention containing a zeolite in acid form, preferably zeolite beta, Cu, and optionally one or more elements selected from elements of groups IIIA, IVA, IIIB, IVB, VB, VIB, VIIB, group VIII limited to Fe, Ru and Os, and of the series of lanthanides, is new and is a further aspect of the present invention.

This catalytic composition preferably contains zeolite beta, Cu and an element selected from Cr and Al. The metals contained in the composition are preferably in the form of oxides. According to a particular aspect of the present invention, copper and chromium are contained in the form of copper chromite.

The copper is preferably contained in the catalytic composition of the present invention in a weight ratio of the metal with respect to the zeolite ranging from 0.001 to 10, more preferably ranging from 0.01 to 2. When the catalytic composition contains one or more elements of groups IIIA, IVA, IIIB, IVB, VB, VIB, VIIB, group VIII limited to Fe, Ru and Os, and of the series of lanthanides, each element is preferably contained in a weight ratio of the metal with respect to the zeolite ranging from 0.001 to 10, more preferably from 0.01 to 2. When the metallic component of the catalytic composition used in this patent comprises copper chromite, Ba and Mn can be present as promoters. These catalytic compositions may additionally contain a binder. The preparation of these catalytic compositions is in accordance with all the methods previously described.

The following examples are provided for a further illustration of the invention without limiting its scope in any way.

EXAMPLE 1

Preparation of the Catalytic System

A catalytic system is prepared, consisting of 10 g of a catalyst based on copper chromite (produced by the company SüdChemie with the trade-name G99b) having the following composition expressed as weight percentage of the elements: Cu 35%, Cr 31%, Ba 2%, Mn 2.5%, indicated hereunder as "material A1" and 4.5 g of a catalyst based on zeolite beta prepared according to the indications described in Example 1 of EP 687500, called "material B1". The zeolite beta used in the preparation of the material B1 is a product of the company Zeolyst with the tradename CP-806 BL 25.

The catalytic system is prepared so that the first zone of said system consists of the material A1 alone in a quantity equal to 3 g and the second zone consists of a mechanical mixture of materials A1 and B1 in a quantity equal to 7 g of material A1 and 4.5 g of material B1. The total quantity of the catalytic system thus prepared is therefore equal to 14.5 g.

EXAMPLE 2

Preparation of the Catalytic System

A catalytic system is prepared, starting from the materials G-99b (57 g)) and zeolite beta (80 g), already used in the previous example, and alumina p-bohemite commercialized by the Company Laroche with the trade-name Versal 450 (143 g).

The materials are mechanically mixed in a ploughshare mixer for about 25 minutes, after which 175 cc of an aqueous solution of acetic acid at 5% w/w are added to the mixture of powders thus obtained, without interrupting the mixing for a further 20 minutes approximately.

The intermediate thus obtained is then subjected to extrusion using a HUTT type gear press extruder and the product thus obtained is subsequently subjected to aging for a time of not less than 48 hours.

After the period of aging, the product, in the form of pellets, is then subjected to calcination treatment in air at a temperature of 550° C. approx. for 5 hours, obtaining a material called "material B2", containing about 25% of material G99b, about 30% of zeolite beta and about 45% of alumina binding carrier.

The catalytic system is prepared so as to consist of a single zone in which there is material B2. The total quantity of catalytic system thus prepared is equal to 9.0 g.

EXAMPLE 3

Preparation of the Catalytic System

A catalytic system is prepared, consisting of two distinct zones, the first of which contains 3 g of material A1 already used in Example 1 and the second containing 8 g of material B2 prepared according to the procedure described in Example 2. The total quantity of catalytic system is therefore equal to 11 g.

EXAMPLE 4

Preparation of the Catalytic System 37 g of a catalyst based on zeolite beta prepared according to the indications provided in Example 1 of EP 687500 (12-16 mesh), are charged into a rotavapor flask having a volume of 500 ml, and are then dried under vacuum at room temperature for 2 hours.

A solution is prepared, consisting of 30.34 g of demineralized water and 8.0 g of copper nitrate, $Cu(NO_3)_2 \cdot 2.5H_2O$ (MW=232.59, 34.4 mmoles). The solid is impregnated at room temperature under vacuum. It is left to slowly rotate, under vacuum for 3 h. It is then dried in an oven for 2 h at 120° C. It is calcined at 316° C./4 h with an increase rate of 1° C. $min^{-1}$.

A second impregnation, as the previous one but using a solution consisting of 4.06 g of Copper nitrate $Cu(NO_3)_2 \cdot 2.5H_2O$ (MW=232.59, 17.5 mmoles) and 15.42 g of demineralized water, is effected on 18.8 g of product, calcined at 316° C.

The solid is impregnated at room temperature under vacuum. It is left to slowly rotate, under vacuum for 3 h. It is dried in an oven for 2 h at 120° C. and is calcined at 482° C./8 h with an increase rate of 1° C. $min^{-1}$.

19.4 g of calcined product are recovered (10.29% Cu).

EXAMPLE 5

Catalytic Test

A catalytic test is carried out, using an experimental apparatus as described below.

The experimental apparatus consists of tanks for the reagents benzene and acetone, feeding pumps of the reagents benzene and acetone, a mass meter for the flow-rate control of hydrogen coming from a cylinder, a static mixer of the reagents before their inlet into the reaction, a preheating unit of the reagents, a steel reactor situated inside an electric heating oven equipped with temperature regulation inside the oven and inside the reactor, a pressure regulation system inside the reactor by means of a pneumatic valve, a cooler of the reaction effluent and a collection system of the liquid and gaseous products.

The reactor, situated inside the heating oven, consists of a steel cylindrical tube, with a mechanical sealing system and internal diameter equal to about 2 cm.

Along the major axis of the reactor there is a thermometer trap having a diameter equal to 1 mm, containing a thermocouple which can run freely along the major axis of the reactor and consequently along the major axis of the catalytic bed.

The catalytic system prepared as described in Example 1 is charged into the reactor, in a quantity equal to 14.5 g, with a size ranging from 1 to 2 mm, for a total height of the catalytic bed equal to 8.5 cm.

A quantity of inert quartz material is charged over and under the catalytic bed for a height equal to 2 cm over and 2 cm under the catalytic bed.

The catalyst is then subjected to drying in a stream of nitrogen at a temperature inside the reactor equal to 160° C. for about 1 hour, and a stream of 5.2 ml/min of low pressure hydrogen is subsequently fed for 60 minutes, followed by a stream of 15.8 ml/min at 180° C. for 120 minutes and finally a stream of 23.6 ml/min at 200° C. for 180 minutes, after which the hydrogen feeding is interrupted and the temperature of the reactor is brought back to a value equal to 150° C., the experimental apparatus being continuously maintained in a stream of nitrogen.

Once a constant temperature of 150° C. has been reached, the stream of nitrogen is then interrupted and the feeding of benzene is initiated with a flow-rate equal to 0.245 ml/min.

The system is maintained under these conditions for 60 minutes, after which the feeding of hydrogen is reactivated at a flow-rate equal to 27.3 ml/min and after a few minutes the feeding of acetone is initiated with a flow-rate equal to 0.012 ml/min.

Approximately 3 hours after the feeding of acetone, samples of reaction effluent are removed, both for the liquid and gaseous part, which are subsequently analyzed by gaschromatography.

Table 1 summarizes the operating conditions, together with the results obtained. In this table:
  WHSV expresses the ratio between the sum of the hourly flow-rates of benzene and acetone (excluding hydrogen) and the quantity of catalytic system;
  the selectivity [aryls]/[acetone] expresses the fraction of acetone converted to cumene+polyisopropylbenzenes (products useful for the production of cumene in transalkylation) with respect to the total quantity of converted acetone;

the selectivity [cumene]/[acetone] expresses the fraction of acetone converted to cumene with respect to the total quantity of converted acetone;

the selectivity [aryls]/[benzene] expresses the fraction of benzene converted to cumene+polyisopropylbenzenes with respect to the total quantity of converted benzene.

EXAMPLE 6

Catalytic Test

A catalytic test is effected, using the same experimental apparatus and the same experimental conditions as Example 5, but charging the catalytic system prepared according to what is described in Example 2, in a quantity equal to 9 g, for a total height of the catalytic bed equal to 8.3 cm. The benzene is fed with a flow-rate equal to 0.184 ml/min.

Approximately 3 hours after the start of the acetone feeding, samples of reaction effluent are removed, both for the liquid and gaseous part, which are subsequently analyzed by gaschromatography.

Table 1 summarizes the operating conditions, together with the results obtained.

EXAMPLE 7

Catalytic Test

A catalytic test is effected, using the same experimental apparatus and the same experimental conditions as Example 5, but charging the catalytic system prepared according to what is described in Example 3, in a quantity equal to 11 g, for a total height of the catalytic bed equal to 8.5 cm. The benzene is fed with a flow-rate equal to 0.251 ml/min.

Approximately 3 hours after the start of the acetone feeding, samples of reaction effluent are removed, both for the liquid and gaseous part, which are subsequently analyzed by gaschromatography.

Table 1 summarizes the operating conditions, together with the results obtained.

EXAMPLE 8

Catalytic Test

A catalytic test is effected, using the same experimental apparatus and the same experimental conditions as Example 5, but charging the catalytic system prepared according to what is described in Example 3, in a quantity equal to 11 g, for a total height of the catalytic bed equal to 8.5 cm. The acetone is fed with a flow-rate equal to 0.009 ml/min, the benzene with a flow-rate equal to 0.072 ml/min.

Approximately 3 hours after the start of the acetone feeding, samples of reaction effluent are removed, both for the liquid and gaseous part, which are subsequently analyzed by gaschromatography.

Table 1 summarizes the operating conditions, together with the results obtained.

EXAMPLE 9

Catalytic Test

A catalytic test is effected, using the same experimental apparatus and the same experimental conditions as Example 5, but charging the catalytic system prepared according to what is described in Example 4, in a quantity equal to 5 g, for a total height of the catalytic bed equal to 5 cm.

The catalyst is then subjected to drying in a stream of nitrogen and the temperature inside the reactor is brought from 120° C. to 190° C. in about 2 hours. Once a constant temperature of 190° C. has been reached, the stream of nitrogen is then interrupted and the feeding of benzene is initiated with a flow-rate equal to 0.254 ml/min. The system is maintained under these conditions for 60 minutes, after which the feeding of hydrogen is reactivated at a flow-rate equal to 27.3 ml/min and after a few minutes the feeding of acetone is initiated with a flow-rate equal to 0.036 ml/min.

Approximately 3 hours after the feeding of acetone, samples of reaction effluent are removed, both for the liquid and gaseous part, which are subsequently analyzed by gaschromatography. Table 1 summarizes the operating conditions, together with the results obtained.

TABLE 1

|  | Example Nr. | | | | |
| --- | --- | --- | --- | --- | --- |
|  | 5 | 6 | 7 | 8 | 9 |
| Quantity of catalytic system (g) | 14.5 | 9 | 11 | 11 | 5 |
| Reaction temperature (° C.) | 150 | 150 | 150 | 150 | 190 |
| Reaction pressure (kpa) | 100 | 100 | 100 | 100 | 100 |
| Total WHSV ($h^{-1}$) | 0.9 | 1.1 | 1.2 | 0.4 | 3.0 |
| [Benz.]/[Acetone] molar ratio | 16.8 | 12.6 | 17.2 | 6.3 | 5.8 |
| [$H_2$]/[Acetone] molar ratio | 7.4 | 7.4 | 7.4 | 9.77 | 2.5 |
| Conversion of acetone % | 100.0 | 100 | 100 | 100 | 98.5 |
| [aryls]/[acetone] selectivity % | 96.6 | 88.3 | 94.6 | 98.0 | 89.1 |
| [cumene]/[acetone] selectivity % | 81.9 | 70.2 | 79.8 | 79.7 | 81.0 |
| [aryls]/[benzene] selectivity % | 99.4 | 96.7 | 99.0 | 99.8 | 96.7 |

EXAMPLE 10

Preparation of the Catalytic System

A material is prepared, consisting of a catalyst based on copper aluminate (produced by SüdChemie under the tradename of T4489, indicated hereunder as "material A2", having the following composition expressed as weight percentage of the elements: Cu 39.3%, Al 15.5%, Zn 6.0%, Mn 6.8%), zeolite beta and alumina p-bohemite. The zeolite beta and alumina are the same materials used in the previous examples.

173 g of alumina, 192 g of zeolite beta, 124 g of T4489 are charged into a ploughshare mixer and mechanically mixed for about 60 minutes, after which 400 cc of an aqueous solution of acetic acid at 2% w/w are added to the mixture of powders thus obtained, without interrupting the mixing for a further 60 minutes approximately.

The intermediate thus obtained is then subjected to extrusion using a HUTT type gear press extruder and the product obtained is then subjected to aging for a period of not less than 48 hours.

After the aging period, the product, in the form of pellets, is subsequently subjected to calcination treatment in air at a temperature of about 550° C. for 5 hours, obtaining a material called "material B3", containing about 30% of copper aluminate T4489, about 40% of zeolite beta and about 30% of an alumina binding carrier. The catalytic system is prepared so that it consists of two distinct zones, the first containing 3 g of the material A2 and the second 7 g of the material B3 prepared as described. The total quantity of catalytic system is therefore equal to 10 g.

EXAMPLE 11

Preparation of the Catalytic System

A material consisting of copper aluminate T4489 and zeolite beta, already used in the previous example, is prepared.

298 g of zeolite beta, 255 g of T4489 are charged into a ploughshare mixer and mechanically mixed for about 60 minutes, after which 365 cc of an aqueous solution of acetic acid at 5% w/w are added to the mixture of powders thus obtained, without interrupting the mixing for a further 60 minutes approximately.

The intermediate thus obtained is then subjected to extrusion using a HUTT type gear press extruder and the product obtained is then subjected to aging for a period of not less than 48 hours.

After the aging period, the product, in the form of pellets, is subsequently subjected to calcination treatment in air at a temperature of about 550° C. for 5 hours, obtaining a material called "material B4", containing about 50% of copper aluminate T4489 and about 50% of zeolite beta. The catalytic system is prepared so that it consists of two distinct zones, the first containing 3 g of the material A2 and the second 7 g of the material B4 prepared as described. The total quantity of catalytic system is therefore equal to 10 g.

EXAMPLE 12

Catalytic Test

A catalytic test is carried out, using the same experimental apparatus described in Example 5.

The catalytic system prepared as described in Example 10 is charged into the reactor in a quantity equal to 10 g, with a size ranging from 1 to 2 mm, for a total height of the catalytic bed equal to 8.5 cm.

A quantity of inert quartz material is charged over and under the catalytic bed for a height equal to 2 cm over and 2 cm under the catalytic bed.

The catalyst is then subjected to drying in a stream of nitrogen for 1 hour during which the internal temperature is brought to 210° C. Once this temperature has been reached, a stream of 1.3 ml/min of benzene is fed for about 30 minutes. The temperature is then lowered to 194° C., the pressure is brought to 2100 Kpa and the nitrogen flow is interrupted. A stream of 367 ml/min of hydrogen is subsequently fed for about 30 minutes. Finally, the benzene feeding is interrupted and a flow of 0.77 g/min of a benzene and acetone solution [C6]/[C3]=6.3, is fed.

About 3 hours after the start of the acetone feeding, samples of effluent are taken from the reaction, both for the liquid and gaseous part, which are subsequently analyzed by means of gaschromatography. Approximately 24 hours after the start of the feeding, the sampling operation is repeated with the same analysis procedure.

Table 2 summarizes the operating conditions, together with the results obtained.

EXAMPLE 13

Catalytic Test

A catalytic test is carried out, using the same experimental apparatus described in Example 5 and under the same experimental conditions as Example 12. The catalytic system prepared as described in Example 11 is charged into the reactor in a quantity equal to 10 g, with a size ranging from 1 to 2 mm, for a total height of the catalytic bed equal to 8.1 cm.

About 3 hours after the start of the acetone feeding, samples of effluent are taken from the reaction, both for the liquid and gaseous part, which are subsequently analyzed by means of gaschromatography. Approximately 24 hours after the start of the feeding, the sampling operation is repeated with the same analysis procedure.

Table 2 summarizes the operating conditions, together with the results obtained.

EXAMPLE 14

Catalytic Test

A catalytic test is carried out, using the same experimental apparatus described in Example 5 and under the same experimental conditions as Example 12, but charging the catalytic system prepared as described in Example 3 in a quantity equal to 11 g for a total height of the catalytic bed equal to 8.3 cm. A flow of 0.76 g/min of a solution of benzene and acetone [C6]/[C3]=6.3, is fed.

About 3 hours after the start of the acetone feeding, samples of effluent are taken from the reaction, both for the liquid and gaseous part, which are subsequently analyzed by means of gaschromatography. Approximately 24, 173 and 384 hours after the start of the feeding, the sampling operation is repeated with the same analysis procedure.

Table 2 summarizes the operating conditions, together with the results obtained.

EXAMPLE 15

Catalytic Test

A catalytic test is carried out, using the same experimental apparatus described in Example 5, but charging the catalytic system prepared as described in Example 3 in a quantity equal to 11 g for a total height of the catalytic bed equal to 8.4 cm.

The catalyst is subjected to drying in a stream of nitrogen at a temperature inside the reactor equal to 160° C. for about 1 hour, after which a flow of 5.2 ml/min of hydrogen is fed at low pressure for 60 minutes, followed by a flow of 15.8 ml/min at 180° C. for 120 minutes and finally a flow of 23.6 nl/min at 200° C. for 180 minutes. The hydrogen feeding is then interrupted and the temperature of the reactor is brought to a value equal to 170° C., the experimental apparatus being maintained in a stream of nitrogen.

Once the temperature has reached a constant value of 170° C., the nitrogen stream is interrupted and the feeding of benzene is initiated with a flow-rate equal to 0.36 ml/min. The pressure is brought to 850 Kpa.

The system is maintained under these conditions for 60 minutes, after which the feeding of hydrogen is restarted at a flow-rate equal to 338 ml/min; after a few minutes, the benzene feeding is interrupted and a flow of 0.76 g/min of a solution of benzene and acetone [C6]/[C3]=6.3, is fed.

About 3 hours after the start of the acetone feeding, samples of effluent are taken from the reaction, both for the liquid and gaseous part, which are subsequently analyzed by means of gaschromatography.

Table 2 summarizes the operating conditions, together with the results obtained.

EXAMPLE 16

Catalytic Test

A catalytic test is carried out, using the same experimental apparatus described in Example 5, but charging the catalytic system prepared as described in Example 3 in a quantity equal to 11 g for a total height of the catalytic bed equal to 8.4 cm.

The catalyst is subjected to drying in a stream of nitrogen for 1 hour during which the temperature inside the reactor is brought to 230° C. Once this temperature has been reached, a flow of 1.3 ml/min of benzene is fed for about 30 minutes. The temperature is then lowered to 210° C., the pressure is brought to 2900 Kpa, the nitrogen stream is interrupted and a flow of 367 ml/min of hydrogen is fed for about 30 minutes. Finally, the benzene feeding is interrupted and a flow of 0.76 g/min of a solution of benzene and acetone [C6]/[C3]=6.3, is fed.

About 20 hours after the start of the acetone feeding, samples of effluent are taken from the reaction, both for the liquid and gaseous part, which are subsequently analyzed by means of gaschromatography.

Table 2 summarizes the operating conditions, together with the results obtained.

TABLE 2

| | Example Nr. | | | | | | | | | | |
|---|---|---|---|---|---|---|---|---|---|---|---|
| | 12 | | 13 | | 14 | | | | 15 | | 16 |
| Time of stream (h) | 3 | 24 | 3 | 24 | 3 | 24 | 173 | 384 | 3 | 24 | 20 |
| Quantity of catalytic system (g) | 10 | 10 | 10 | 10 | 11 | 11 | 11 | 11 | 11 | 11 | 11 |
| Reaction temperature (° C.) | 194 | 194 | 194 | 194 | 194 | 194 | 194 | 194 | 174 | 174 | 210 |
| Reaction pressure (kpa) | 2100 | 2100 | 2100 | 2100 | 2100 | 2100 | 2100 | 2100 | 850 | 850 | 2900 |
| Total WHSV ($h^{-1}$) | 4.6 | 4.6 | 4.6 | 4.6 | 4.1 | 4.1 | 4.1 | 4.1 | 4.1 | 4.1 | 4.1 |
| [Benz.]/[Acetone] molar ratio | 6.3 | 6.3 | 6.3 | 6.3 | 6.3 | 6.3 | 6.3 | 6.3 | 6.3 | 6.3 | 6.3 |
| [$H_2$]/[Acetone] molar ratio | 11.9 | 11.9 | 11.9 | 11.9 | 11.9 | 11.9 | 11.9 | 11.9 | 10.8 | 10.8 | 11.9 |
| Conversion of acetone (%) | 100.0 | 100.0 | 100.0 | 100.0 | 100.0 | 100.0 | 100.0 | 100.0 | 100.0 | 100.0 | 100.0 |
| [Aryls]/[Acetone] selectivity (%) | 97.8 | 97.8 | 97.6 | 97.8 | 97.7 | 97.8 | 97.7 | 97.0 | 97.1 | 96.2 | 96.9 |
| [Cumene]/[Acetone] selectivity (%) | 76.6 | 76.7 | 73.9 | 73.7 | 76.9 | 77.0 | 76.8 | 76.2 | 68.7 | 70.1 | 83.8 |
| [Aryls]/[Benzene] selectivity (%) | 98.8 | 99.0 | 98.7 | 98.8 | 99.2 | 99.3 | 99.3 | 99.1 | 99.6 | 99.3 | 99.2 |

The invention claimed is:

1. A catalytic composition, comprising:
   a zeolite in acid form, Cu and one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series;
   wherein when the element is chromium, copper and chromium are at least in part in the form of copper chromite and when the element is aluminum, copper and aluminum are at least in part in the form of copper aluminate.

2. The catalytic composition according to claim 1, comprising:
   a zeolite in acid form, Cu and one or more elements selected from Al and Cr, wherein when the element is chromium, copper and chromium are at least in part in the form of copper chromite and when the element is aluminum, copper and aluminum are at least in the form of copper aluminate.

3. The catalytic composition according to claim 1, comprising a zeolite in acid form, selected among zeolite beta, zeolite ZSM-12 and mordenite; Cu and one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series.

4. The catalytic composition according to claim 1, comprising zeolite Y in acid form, Cu, and one or more elements selected from the group consisting of an element of Group IIIA, an element of Group IVA, an element of Group IIIB, an element of Group IVB, an element of Group VB, an element of Group VIIB, Fe, Ru, Os, and an element of the lanthanide series.

5. The catalytic composition according to claim 1, further comprising a binder.

6. The catalytic composition according to claim 1, wherein the zeolite is zeolite beta.

7. A process for preparing the catalytic composition according to claim 1, comprising impregnating the zeolite with an aqueous solution containing a copper salt and a salt of one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series, to form a product, and drying and calcining the product.

8. The process according to claim 7, wherein the resulting product is bound with an inorganic binder.

9. A process for preparing the catalytic composition according to claim 1, comprising impregnating the zeolite and one or more inorganic binders with an aqueous solution containing a copper salt and a salt of one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series, to form a product, and drying and calcining the product.

10. A process for preparing the catalytic composition according to claim 1, comprising performing an ionic exchange of the zeolite with an aqueous solution containing a copper salt and a salt of one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series, and drying and calcining the product.

11. The process for preparing the catalytic composition according to claim 10, wherein the product obtained is bound with a binder.

12. A process for preparing the catalytic composition according to claim 1, comprising performing an ionic exchange of a composition of zeolite and suitable binding agents with an aqueous solution containing a copper salt and a salt of one or more elements selected from the group consisting of an element of Group IIIA, an element of Group IVA, an element of Group IIIB, , an element of Group IVB, an element of Group VB, an element of Group VIB, an element of Group VIIB, Fe, Ru, Os, and an element of the lanthanide series, to form a product, and drying and calcining the product.

13. A process for preparing the catalytic composition according to claim 1, comprising extruding, drying and calcining a mechanical mixture, paste-mixed with a peptizing agent, of the zeolite, Cu, and one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series, in the form of oxides.

14. A process for preparing the catalytic composition according to claim 1, comprising extruding, drying and calcining a mechanical mixture, paste-mixed with a peptizing agent, of the zeolite, Cu, and one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series, in the form of oxides, and one or more inorganic binders.

15. A process for preparing the catalytic composition according to claim 1, comprising assembling various distinct zones, each comprising a metallic component, or a zeolitic component, or a combination of both components, and wherein the metallic component comprises copper and one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series.

16. A catalytic composition, comprising:

a zeolite in acid form;

copper;

one or more elements selected from the group consisting of an element of Group IIIA, an element of Group IVA, an element of Group IIIB, an element of Group IVB, an element of Group VB, an element of Group VIB, an element of Group VIIIB, Fe, Ru, Os, and an element of the lanthanide series; and chromium;

wherein at least a portion of the copper and the chromium are present in the form of copper chromite.

17. A catalytic composition, comprising:

a zeolite in acid form;

copper;

one or more elements selected from the group consisting of an element of Group IIIA, an element of Group IVA, an element of Group IIIB, an element of Group IVB, an element of Group VB, an element of Group VIB, an element of Group VIIB, Fe, Ru, Os, and an element of the lanthanide series; and aluminum;

wherein at least a portion of the copper and the aluminum are in the form of a copper aluminate.

* * * * *